US009541492B2

(12) United States Patent
Howard et al.

(10) Patent No.: US 9,541,492 B2
(45) Date of Patent: Jan. 10, 2017

(54) METHOD AND APPARATUS FOR STABILIZING THE THICKNESS OF AN OPTICAL CHANNEL FOR EXTENDED PRESSURE ENVIRONMENTS

(71) Applicant: The United States of America, as represented by the Secretary of the Navy, Washington, DC (US)

(72) Inventors: Paul L. Howard, Newmarket, NH (US); John E. Tucker, Centreville, VA (US); John F. Reintjes, Alexandria, VA (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 14/727,754

(22) Filed: Jun. 1, 2015

(65) Prior Publication Data
US 2015/0346081 A1 Dec. 3, 2015

Related U.S. Application Data

(60) Provisional application No. 62/004,955, filed on May 30, 2014.

(51) Int. Cl.
*G01N 21/05* (2006.01)
*G01N 21/11* (2006.01)
(Continued)

(52) U.S. Cl.
CPC .......... *G01N 21/05* (2013.01); *G01N 15/0227* (2013.01); *G01N 21/11* (2013.01);
(Continued)

(58) Field of Classification Search
CPC .... G01N 21/05; G01N 21/03; G01N 21/0303; G01N 30/74; G01N 21/031
(Continued)

(56) References Cited

U.S. PATENT DOCUMENTS 2,594,113 A * 4/1952 Askin ............... F25B 41/006
116/276
3,187,573 A * 6/1965 Goellner ............. G01F 23/02
73/293

(Continued)

OTHER PUBLICATIONS

International Search Report and Written Opinion of the International Searching Authority, PCT/US2015/033617, dated Oct. 28, 2015.

*Primary Examiner* — Tarifur Chowdhury
*Assistant Examiner* — MD M Rahman
(74) *Attorney, Agent, or Firm* — US Naval Research Laboratory; Sally A. Ferrett

(57) ABSTRACT

A high pressure optical flow cell system suitable for use in a real time optical particle monitoring system. The system is modular, with at least two housings joined together with removable mechanical attachment devices. Inlet and outlet passageways introduce and remove high pressure fluid into a flow cavity located between adjacent housing faces. An o-ring or other compliant member seal is provided between the faces to prevent leaks of the high pressure fluid. At least one optical window is provided with a substantially planar face flush with the flow cavity surface. An optical assembly maintains the face of the optical window flush with the flow cavity surface over a wide range of temperatures and pressures. A system and method for maintaining the face of the optical window flush with the flow cavity surface over a wide range of temperatures and pressures.

25 Claims, 14 Drawing Sheets

(51) Int. Cl.
*G01N 33/28* (2006.01)
*G01N 15/02* (2006.01)
*G01N 21/03* (2006.01)
*G01N 15/00* (2006.01)

(52) U.S. Cl.
CPC ..... *G01N 33/2858* (2013.01); *G01N 33/2888* (2013.01); *G01N 21/0317* (2013.01); *G01N 2015/0053* (2013.01); *G01N 2021/0389* (2013.01)

(58) Field of Classification Search
USPC .......................................................... 356/246
See application file for complete search history.

(56) References Cited

U.S. PATENT DOCUMENTS

| | | | |
|---|---|---|---|
| 4,422,323 A * | 12/1983 | Linder | F02B 77/085 73/114.09 |
| 4,705,339 A * | 11/1987 | Hayes | H01R 13/432 439/277 |
| 5,187,768 A * | 2/1993 | Ott | G02B 6/266 385/140 |
| 5,572,320 A | 11/1996 | Reintjes et al. | |
| 5,676,448 A * | 10/1997 | Urbaing | B64F 1/20 362/153.1 |
| 6,049,381 A | 4/2000 | Reintjes et al. | |
| 6,104,483 A | 8/2000 | Sebok et al. | |
| 7,758,104 B2 * | 7/2010 | Liebl | B60J 5/02 296/146.2 |
| 7,921,739 B2 | 4/2011 | Fjerdingstad et al. | |
| 8,056,400 B2 | 11/2011 | Reintjes et al. | |
| 8,582,100 B1 | 11/2013 | Tucker et al. | |
| 8,654,329 B2 | 2/2014 | Tucker et al. | |
| 2005/0287422 A1 | 12/2005 | Kim et al. | |
| 2006/0096353 A1 | 5/2006 | Hawkes et al. | |
| 2007/0064226 A1 | 3/2007 | Kolp et al. | |
| 2010/0027006 A1 | 2/2010 | Hertens et al. | |

* cited by examiner

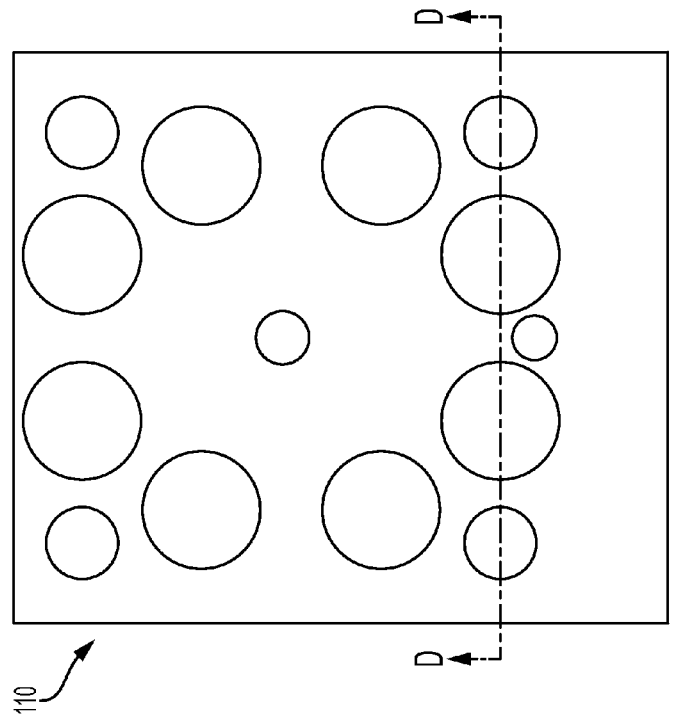
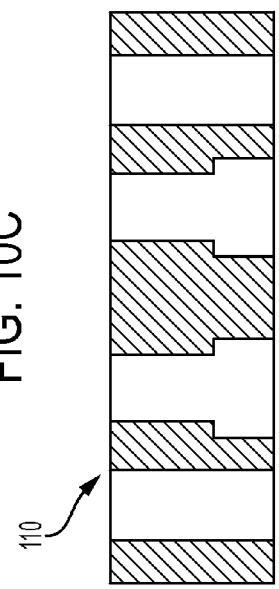
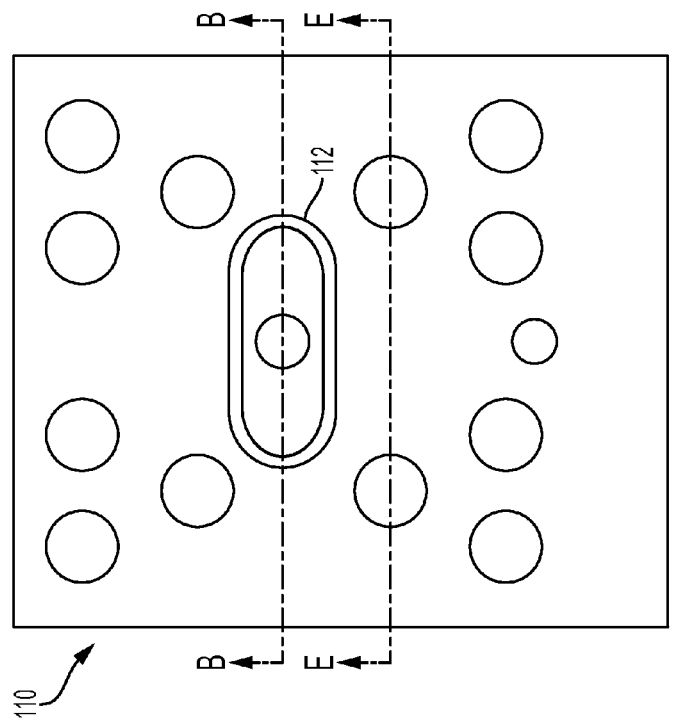
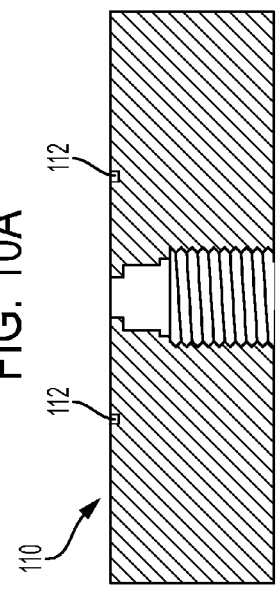

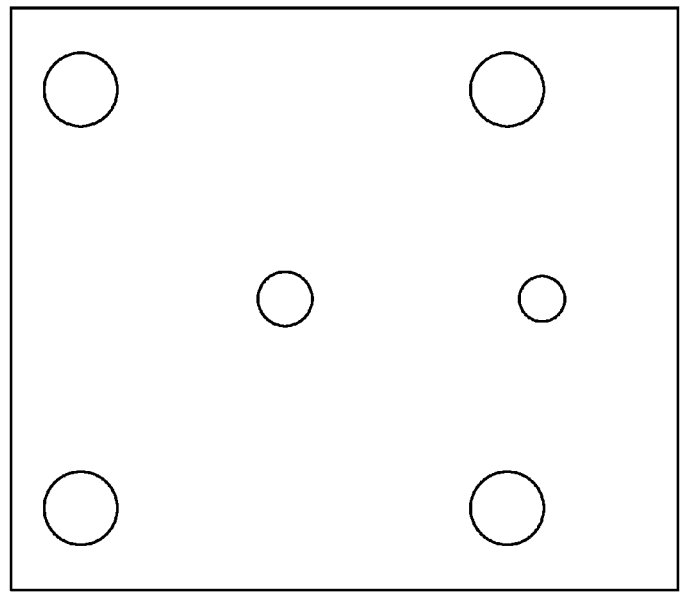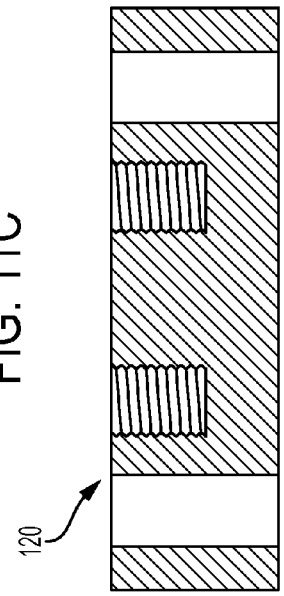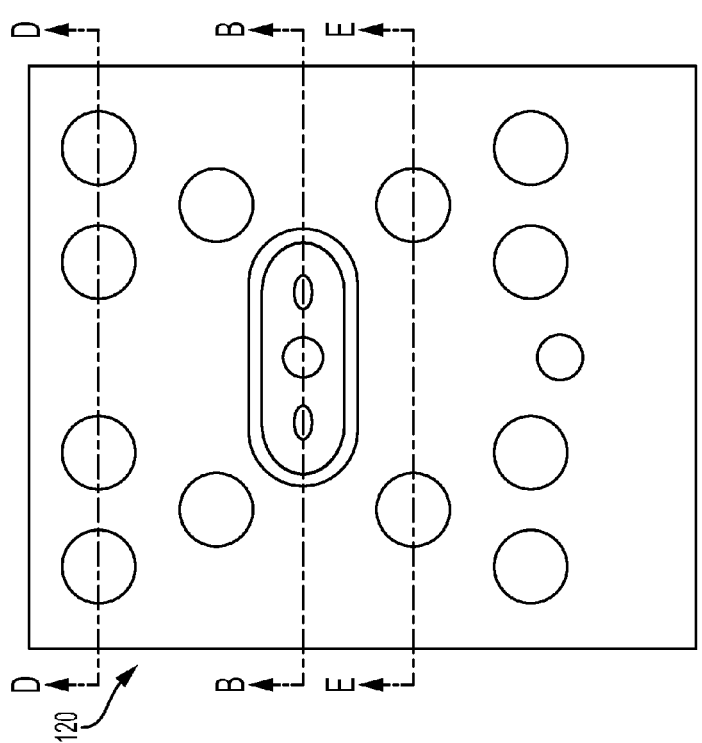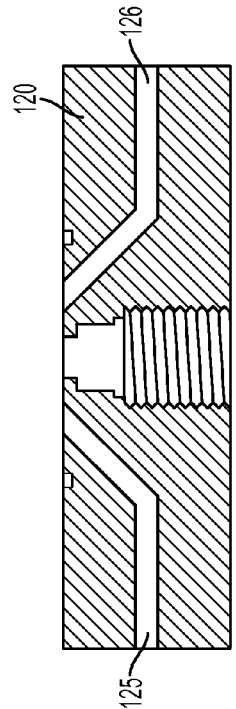

METHOD AND APPARATUS FOR STABILIZING THE THICKNESS OF AN OPTICAL CHANNEL FOR EXTENDED PRESSURE ENVIRONMENTS

CROSS-REFERENCE TO RELATED APPLICATIONS

This Application is a non-provisional under 35 USC 119(e) of, and claims priority to Application 62/004,955 filed on May 30, 2014 in the United States.

BACKGROUND

1. Technical Field

This is related to systems for optically monitoring objects suspended in flowing fluid, and more particularly, to particle monitoring systems for monitoring the presence and size of debris in hydraulic fluid or in lubricants such as oil.

2. Related Technology

U.S. Pat. No. 5,572,320 to Reintjes et al. and U.S. Pat. No. 6,049,381 disclose in-situ fluid samplers for identifying particles in a flowing fluid with an optical near-field imaging device. U.S. Pat. No. 6,049,381 to Reintjes et al. discloses a real time suspended particle monitor that uses a pulsed collimated optical source to produce a series of images of particles in a flowing fluid. U.S. Pat. No. 7,921,739 to Fjerdingstad et al. discloses a real-time optical monitoring system having an automatic on line bottle sampling operation.

U.S. Pat. No. 8,056,400 to Reintjes et al. discloses a system for particle entrained fluid sampling in a high pressure or high flow rate fluid flow system.

U.S. Pat. No. 8,582,100 to Tucker et al. and U.S. Pat. No. 8,654,329 to Tucker et al. discloses systems with series and parallel optical particle sensors for optically monitoring debris and other particles in flowing fluid systems.

BRIEF SUMMARY

A high pressure cell for viewing high pressure fluid passing through the cell, comprising: a first housing member and a second housing member; a spacer member sandwiched between substantially planar surfaces of the first housing member and the second housing member, the spacer member having a thickness less than the first and second housing members, the spacer member having hole therethrough with an edge of the hole defining a flow cavity between the first housing member and the second housing member; each of the first housing member and the second housing member having a groove for a gasket on a surface of the housing member that faces the spacer member, each groove surrounding and being larger than the hole through the spacer member; an inlet passage formed in either the first housing member or the second housing member extending from an outer face of the first or second housing member to the flow cavity; an outlet passage formed in either the first housing member or the second housing member and extending from an outer face of the first or second housing member to the flow cavity; and an optical window in a mounting hole of the first housing member positioned with a surface of the optical window exposed to the flow cavity.

A method for illuminating high pressure flowing fluid in a high pressure cell, comprising: providing the high pressure cell, including a first housing member and a second housing member, a spacer member held tightly between substantially planar surfaces of the first housing member and the second housing member, the spacer member having a thickness less than the first and second housing members, the spacer member having a hole therethrough with an edge of the hole defining a flow cavity between the first housing member and the second housing member, each of the first housing member and the second housing member having a groove for a gasket on a surface of the housing member that faces the spacer member, each groove surrounding and being larger than the hole through the spacer member, an inlet passage formed in either the first housing member or the second housing member extending from an outer face of the first or second housing member to the flow cavity, an outlet passage formed in either the first housing member or the second housing member and extending from an outer face of the first or second housing member to the flow cavity, and an optical window in a mounting hole of the first housing member positioned with a surface of the optical window exposed to the flow cavity; introducing high pressure fluid into the flow inlet such that the fluid flows through the flow cavity and exits through the flow outlet; and directing light through the optical window into the high pressure fluid in the flow cavity.

A system for maintaining the end surface of an optical window at the surface of a surrounding housing member, comprising: a housing member having a first surface, a second opposite surface, and a mounting hole extending from the first surface to the second opposite surface for receiving the optical window, the mounting hole having a cross sectional area that is smaller near the first surface of the housing and larger near the second opposite surface of the housing; an optical window having a first end portion with a substantially constant smaller cross sectional area, a second end portion with a substantially constant larger cross sectional area, and a outwardly extending shoulder between the first and second end portions; the optical window positioned in the mounting hole with the smaller end portion of the housing facing the first surface of the housing; a compliant gasket fitting around the first end portion of the window between the shoulder portion of the window and a corresponding first shoulder surface in the mounting hole; and an externally threaded retaining member positioned in a larger cross sectional threaded portion of the mounting hole, such that tightening the retaining member compresses the gasket against the first shoulder of the mounting hole, creating a static seal and positioning the window with the first end face in a desired axial position with respect to the first surface of the housing.

Additional details will be apparent from the drawings listed below and the detailed description.

BRIEF DESCRIPTION OF THE DRAWINGS

FIG. 10A-10E show different views of a first housing member.

FIG. 11A-11E show different views of a second housing member.

DETAILED DESCRIPTION OF EMBODIMENTS OF THE INVENTION

Figure 1:
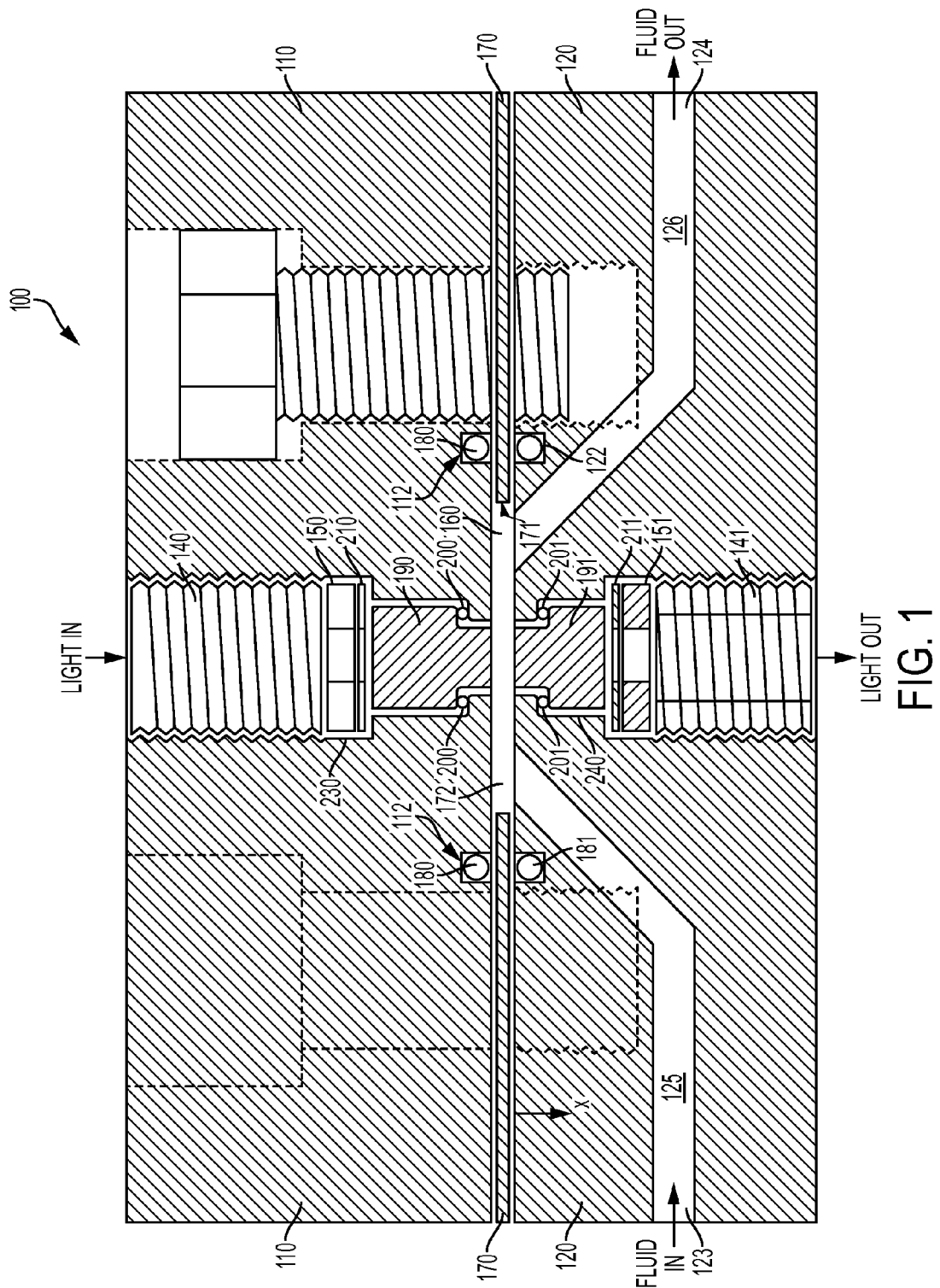
FIG. 1 is a cross sectional view of an example of a high pressure fluid flow system designed for optical viewing of the flow at high pressure.

FIG. 1 illustrates an exemplary high pressure fluid flow optical viewing cell device 100. Two high strength housings 110 and 120 and an optional prism housing are held together by a screw/thread arrangement or other mechanical clamping system (not shown). A cavity is formed between the two high strength housings. The cavity has optically transparent windows on each of two opposed sides.

In operation, high pressure fluid enters the cavity, passes through the cavity, and exits the device. Light enters the cavity through one of the optical windows in a direction perpendicular to the fluid flow, passes through the fluid cavity, and exits the device. As the fluid travels through the cavity, a light source directs light into the fluid through one of the optical windows, through the fluid, through the opposite window, and to an imaging device located external to the device 100 (not shown). In a preferred embodiment, the light is coherent laser light. The imaging device captures images of particles in the fluid as the fluid passes between the optical windows. The resulting image or sequence of images can be used to determine the number, size, and type of particles in the fluid, and other useful information. In operation, the light can be a coherent laser light, with a wavelength suitable for imaging particles in the fluid as the fluid passes through the cavity.

Figure 2:
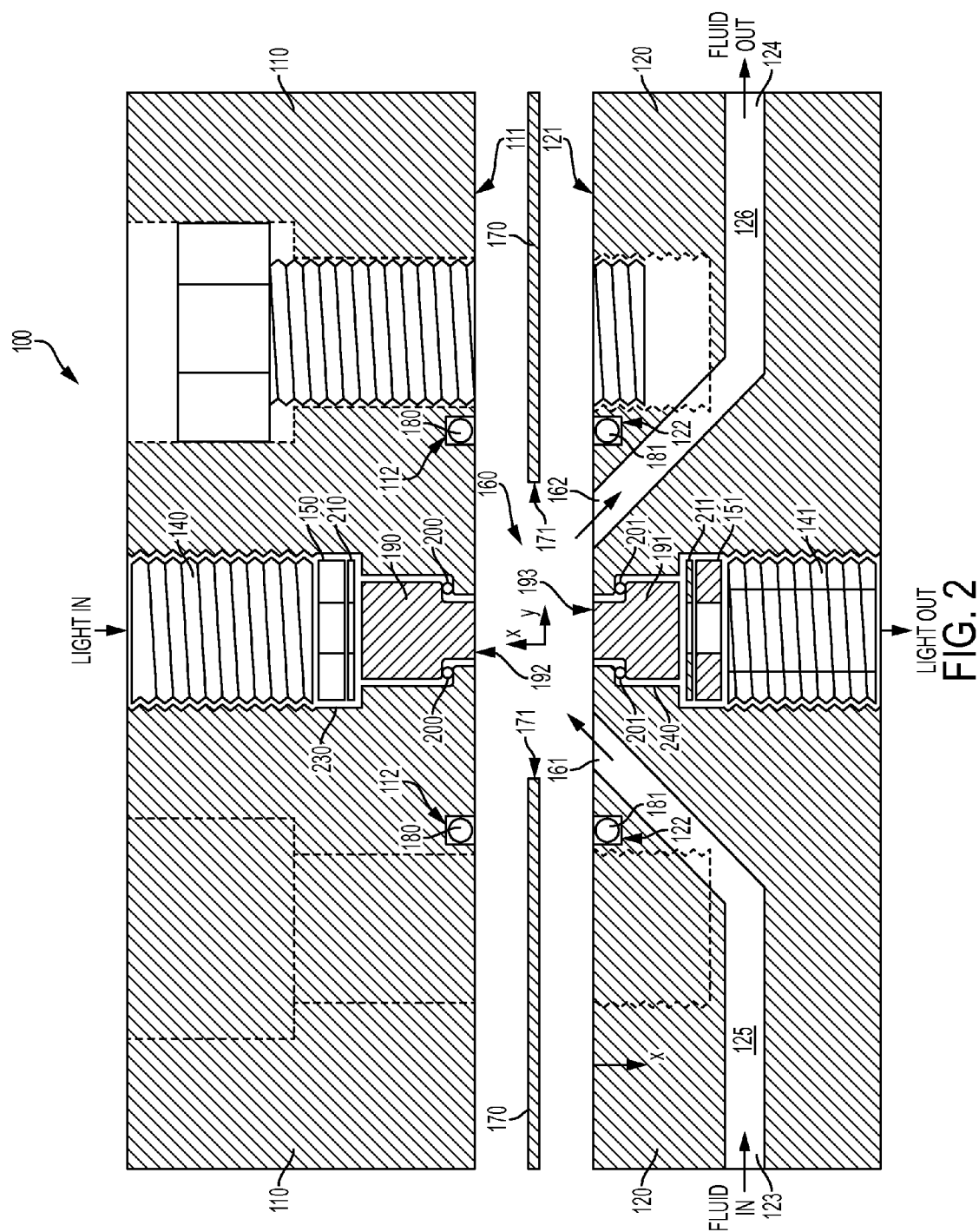
FIG. 2 is another view of the high pressure fluid flow system, with the housing components slightly separated to illustrate the gap spacer or shim characteristics.

FIG. 2 shows the components of an exemplary high pressure fluid flow optical viewing cell device, in a cross section taken at a plane through the optical flow path and the fluid flow path, with the housing members shown spaced apart from each other to illustrate the details of the flow cavity 160.

An optical cell spacer, or "shim", 170 is positioned between the two housing sections 110 and 120 and is held tightly between the housing sections by the pressure imparted by the mechanical screw/thread arrangement or other mechanical clamping system. The shim has a hole 172 extending through the shim at a generally central location aligned with the optical windows. A cavity 160 is formed between the inner faces 111, 121 of the housings 110 and 120 and the circumferential edge 171 of the hole 172 in the shim 170. The high strength housings 110 and 120 have inside faces 111 and 112, respectively, that face toward the shim 170. Each of the faces 111, has an o-ring groove 112, 122 for holding each o-ring gasket 180, 181 between the housing face and the shim 170. When the system is assembled and held together by the mechanical clamping system, the o-rings seal the cavity 160 so high pressure fluid does not escape from between the shim and the housings 110 and 120.

As discussed further in later paragraphs, the housing 110 and 120 are mechanically attached to each other in such a manner as to prevent flow past the o-ring gaskets 180, 181. The housings and mechanical attachments can also be designed to minimize any distortion in the x direction, as will be discussed in later paragraphs.

One of the housing sections 120 includes fluid passageways for high pressure fluid to enter the cavity and exit the cavity. An inlet passageway 125 has an inlet port 123 for receiving a high pressure flowing fluid, with the inlet passageway extending from the inlet port to an opening 161 to the cavity 160 at the inner face 121 of the housing section 120. The housing section 120 also includes an outlet port 124 and an outlet passageway 126 extending from an opening 162 at the cavity 160 to the outlet port 124.

As seen in FIGS. 1 and 2, each of the fluid passageways 125, 126 can have a horizontal portion and a slanted portion. This shape allows each passageway to be machined in two steps such the passageway meets the housing at the side face at an approximately perpendicular angle to allow a standard connector to be used, and with an oblique angle at the inner faces 121, 111. An oblique angle is formed where the horizontal sections and the slanted sections of the passageway meet within the housing. This also allows the fluid to enter and exit the flow cavity 160 at openings 161, 162 an oblique angle, rather than perpendicular to the direction of flow. The oblique angle is believed to allow more entrained particles to more readily pass out of the cavity with the fluid flow without collecting or recirculating within the cavity.

Figure 3A:
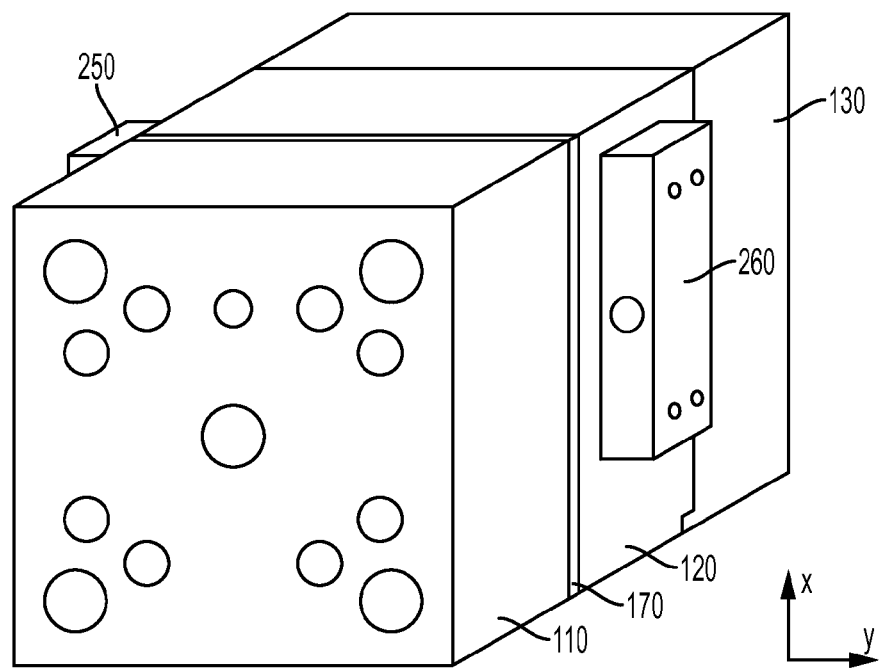
FIGS. 3A and 3B are views of the assembled system.
Figure 3B:
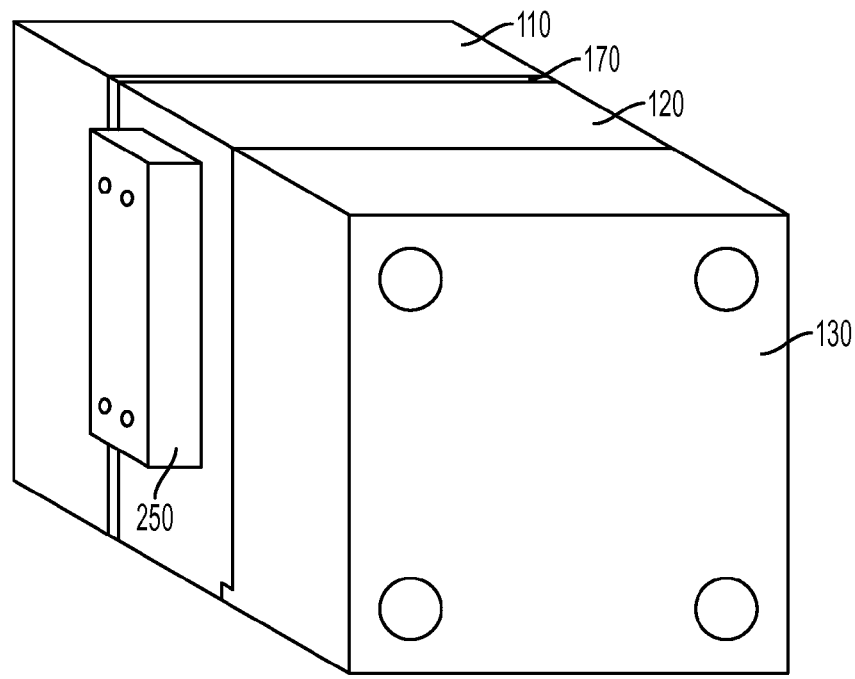
Figure 4A:
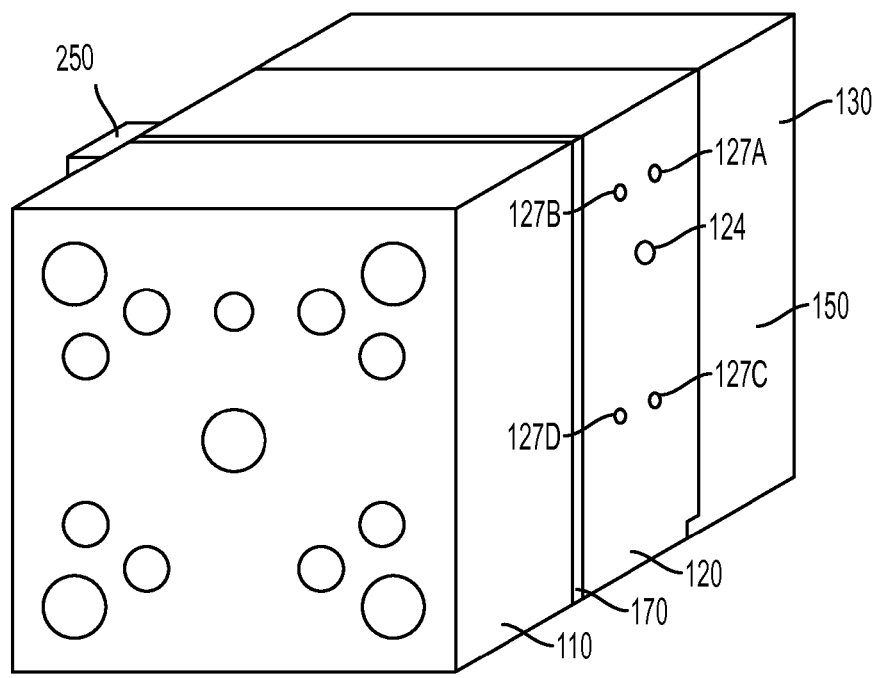
FIGS. 4A and 4B are views of the assembled system without the optional flow direction adapters.
Figure 4B:
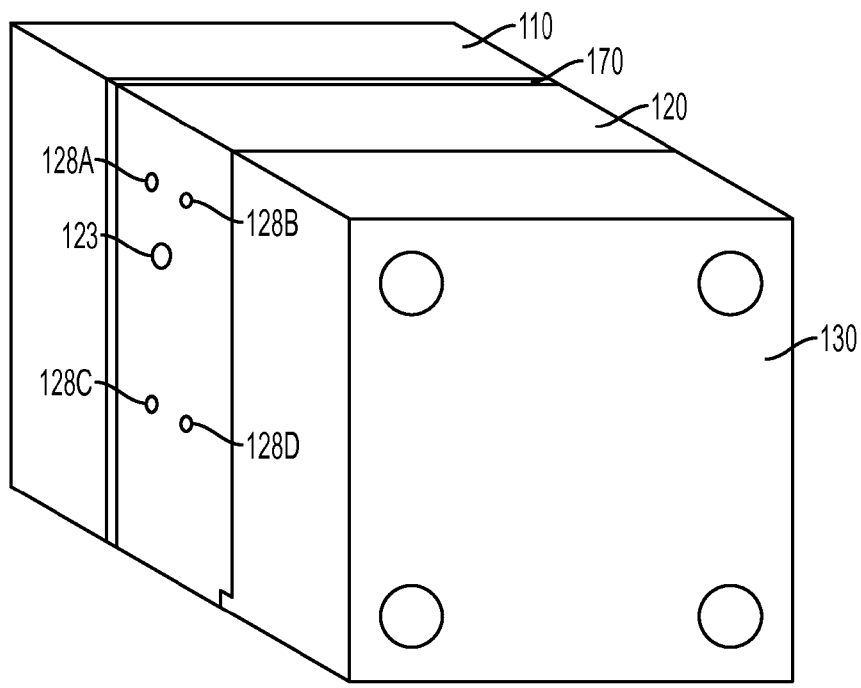

FIGS. 3A and 3B illustrate the assembled system with the addition of optional inlet and outlet flow adapter structures 250 and 260 that can direct the fluid flow to and from the fluid-carrying system to be monitored (e.g., a hydraulic fluid system, a lubricating oil system, etc.). FIGS. 4A and 4B illustrate the assembled system from a front view and a rear view with the flow adapter structures removed. Note that the internally threaded holes 127A-D and 128A-D for receiving connecting screws or bolts that hold the flow adapter structure in place are shown at the side faces of housing 120 in FIGS. 4A and 4B.

Figure 4C:
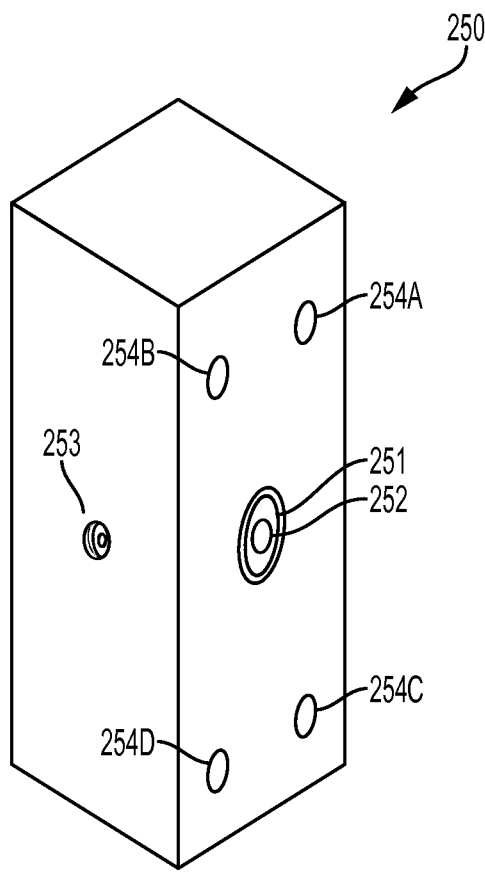
FIGS. 4C and 4D are additional views of one of the optical flow direction adapters.
Figure 4D:
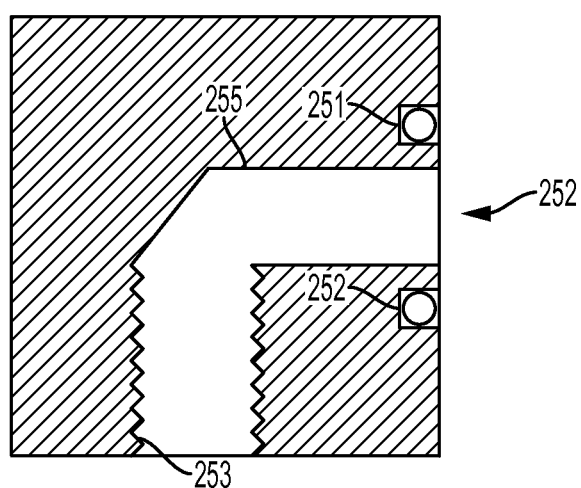

FIGS. 4C and 4D illustrate one of the flow adapter structures 250. The surface that faces the housing 120 has an opening 252 that corresponds to the input port 123 of the housing 120. An o-ring groove and o-ring keep are provided around the opening 252 to prevent leakage. Four bolt holes 254A, 254B, 254C, and 254D are provided to allow bolts to connect the flow adapter structure to the housing 120 at the threaded connection holes 128A, 128B, 128C, and 128D. A passageway 255 extends through the structure 250 to an adjacent face, where a threaded opening 253 can be positioned. The threaded opening 253 can be of any suitable type that can interface with an external fluid connector.

Note that the flow adapter structures 250 and 260 are optional, and can be of various configurations depending on the overall system flow design. The adapters shown herein allow the fluid to enter and exit the system at the same side of the device 100.

Figure 5A:
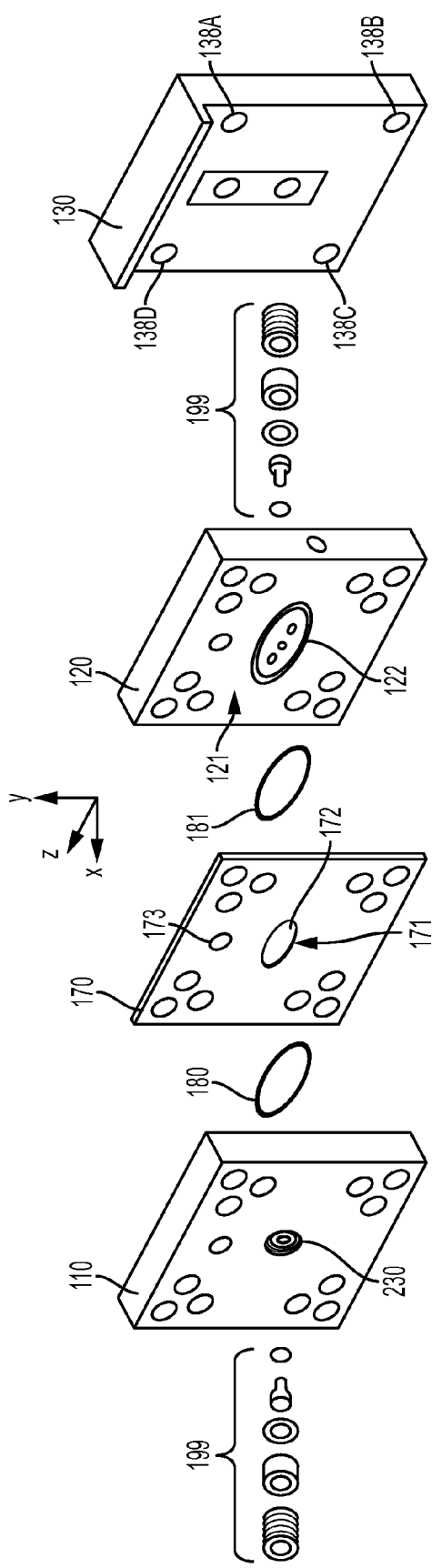
FIGS. 5A and 5B show the housing, shim, and optical components in an exploded views.
Figure 5B:
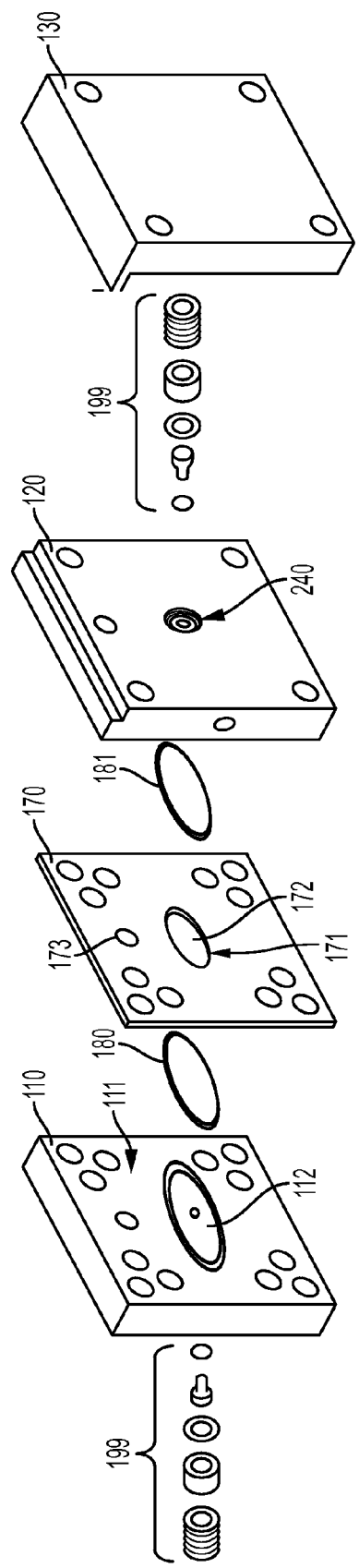

FIGS. 5A and 5B show the housings, shim, and the optical assembly components in an exploded view.

The o-rings 180, 181 sizes and shapes correspond to the o-ring grooves 112, 122 in the faces of the housings 110, 120. In this example, the o-rings and grooves have an oval or racetrack shape that is sized slightly larger than the inside edge of the hole 172 through the shim 170, which defines the size and shape of the flow cavity. The elongated shape is intended to allow the fluid flow through the cavity to flow generally directly from the inlet to the outlet, while minimizing the overall size of the flow cavity in the y cross-flow direction. Other shapes for the flow cavity, and for the o-rings and grooves can also be suitable. The o-ring material is preferably one that resists degradation by the fluid to which it is exposed. VITON can be a suitable choice, although other alternatives can be selected based on the application.

Recall that the system includes optical windows 190, 191 positioned on opposite sides of the cavity 160 that is formed between the inner surfaces 111, 121 of the housings 110, 120. The optical windows 190, 191 have substantially planar surfaces 192, 193 that are flush with the inner surfaces 111, 121 of the housings 110 and 120 on opposite sides of the fluid cavity 160. The optical window faces 192, 193 are not obstructed with respect to the fluid flow and are free of any mechanical or adhesive attachment between the optical window faces and the housing faces 111, 121. The design shown herein keeps the optical window surfaces in an unobstructed position flush with the cavity surface with little or no axial movement even under high pressure flow. In particular, the optical assemblies 199 can also include threaded retainers 140, 141, spacers 150, 151, washers 210, 211, and compliant members 200, 201 that fit against shoulders in a corresponding central opening in the housings 110 and 120.

Figure 6:
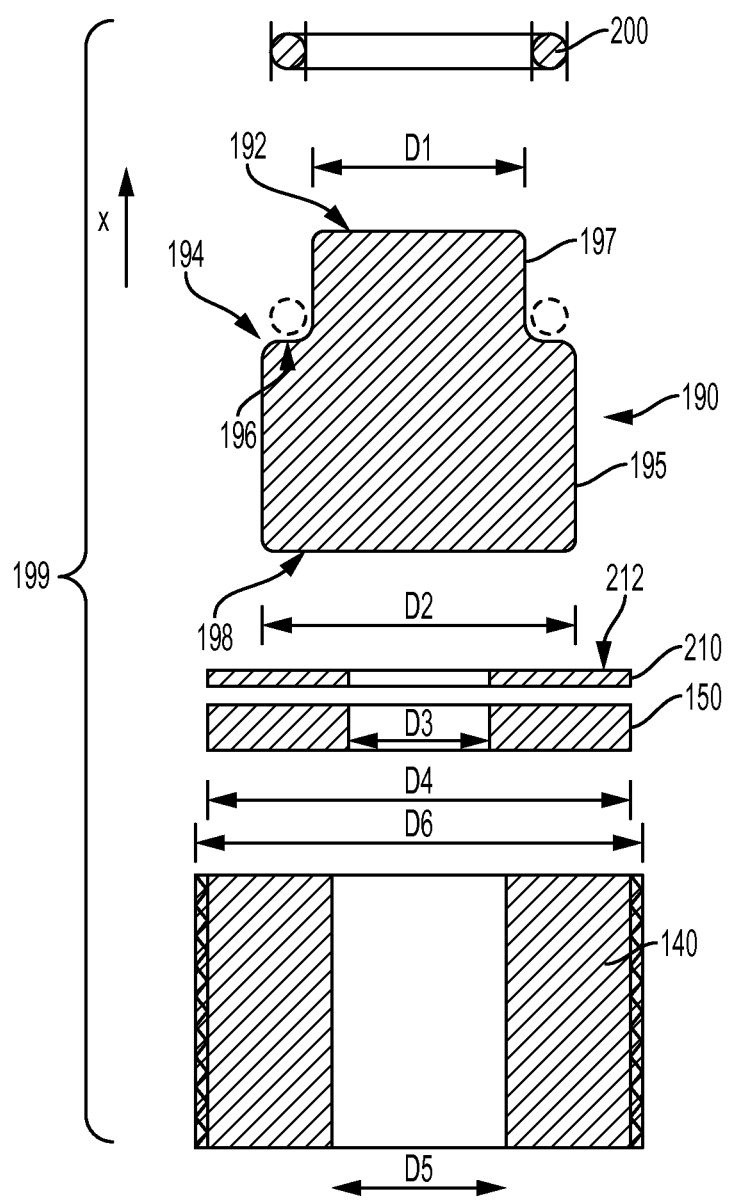
FIG. 6 is a cross sectional view of the optical assembly components in more detail.

FIG. 6 shows the optical system components of an optical assembly 199 in more detail. Because in an exemplary embodiment, the optical assemblies on either side of the fluid cavity 160 are substantially the same, only one is shown. However, it may be suitable in other applications to have different optical assembly designs on the opposed sides of the cavity.

The optical window 190 is formed of a material that is transparent at the wavelength of the light source, and can be, for example, fused silica glass, or another glass or glass-like material.

In this example, the window 190 is cylindrical in cross section, with a smaller-diameter portion 197 at the end that is closest to the flow cavity. The smaller diameter portion 197 is of approximately constant diameter, with a substantially planar polished end surface 192. The window 190 has a larger diameter portion 195 at the other end, with an approximately constant diameter and a substantially planar polished end surface 198. A shoulder portion 194 connects the smaller and larger diameter portions. The shoulder portion 194 should have a radius of curvature large enough to minimize the chance of crack propagation, and should have an approximately flat surface 196 extending radially outward from the smaller diameter portion 197, so a gasket such as an o-ring 200 can be seated between the window flat surface 196 and a corresponding shoulder in the hole 230 in the housing 110.

The compliant members 200, 201 can be gaskets such as o-rings that are formed of a suitable elastomeric material that is resistant to degradation by fluids such as oil or hydraulic fluid. One suitable material is a synthetic rubber and fluoropolymer elastomer (fluoroelastomer) available from DuPont Performance Elastomers L.L.C. under the brand name VITON. Each of the compliant members 200, 201 has an inner diameter sized to have a close fit with the outside of the smaller-diameter cylindrical end portion 197 of the window 190. The compliant member forms a seal to keep the high pressure fluid from leaking through the small space between the outside of the window 190, 191 and the inner surface of the hole 230, 240 in the housing 110, 120.

In other examples, the window has a different cross sectional profile than circular. For example, the cross sectional shape of the window 190, 191 can be, for example, rectangular or square. Both of the holes 230, 240 in the housings will have a corresponding cross sectional shape, e.g., rectangular or square, and the compliant gasket 200, 201 that surrounds the smaller cross sectional dimension portion of the window will have a corresponding shape such that the gasket is seated between a flat surface of the window and the hole in the housing to prevent leakage of the high pressure fluid.

An optional washer 210, 211, can be positioned at the far end of the window opposite the flow passageway. The washer can be very thin, and formed of a relatively compliant material such as, for example, a plastic sheet made from the resin polyethylene terephthalate (PET), available under the tradename MYLAR from Dupont.

A spacer 150 can be positioned on the opposite face of the washer 210, or can be positioned directly at the face 198 of the window 190 if no washer is present. The spacer 150 is thicker than the washer 210, and can be formed of a material that is somewhat stiffer than the washer. One suitable material is a polyamide-imide, a high strength plastic with a very high strength and stiffness, available under the tradename TORLON PAI from Solvay Plastics.

Both the washer 210, 211 and the spacer 150, 151 have an outer width dimension D4 that is slightly smaller than the corresponding width of the hole at that position, and larger than the widest portion 195 of the window 190. Both the washer and the spacer have an inner width dimension D3 that allows the laser light to pass axially through central holes in the washer and spacer to the window 190.

In some examples, the hole through the center of the washer and spacer is circular, and the inner width dimension D3 is a diameter. In other examples, the hole through the center of the washer and spacer has another cross sectional shape, such as a square or hexagonal shape. In those examples, the inner width dimension D3 is a representative dimension such as the length of the sides of a square or the diameter of a circle through the inside, outside, or center points of the hexagon. It may also be suitable to have the spacer and washer to have unequal inside width dimensions.

Figure 7:
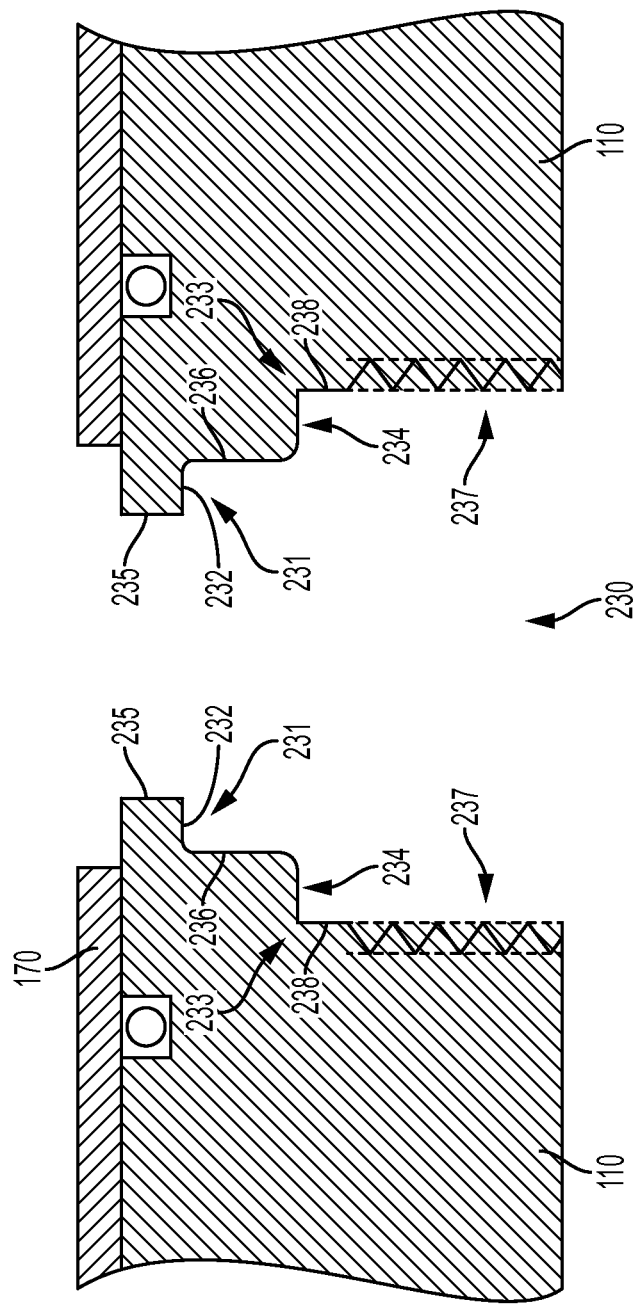
FIG. 7 shows the mating hole in one of the housings that holds the optical assembly in place.

FIG. 7 illustrates the shape of exemplary holes 230, 240 in the housings 110, 120 that receive the optical assemblies. In this example, the optical assemblies and the holes are identical for housing 110 and 120, so only the portion of housing 110 is shown for convenience. A first hole portion 235 extends perpendicularly from the opening at the face of the housing 110, with across sectional dimension slightly larger than the cross sectional dimension D1 of the window 190, and the length of this portion is approximately equal to the length of the smaller area portion 197 of the window 190. A first shoulder 231 provides a flat surface 232 against which the compliant gasket member 200 is compressed. A second, wider portion 236 of the hole 230 has a cross sectional dimension slightly larger than the washer and spacer dimension D4. Another shoulder 233 provides a flat surface 234 against which the washer 210 (if present) and spacer 150 are pressed by the retainer 140. An internally threaded cylindrical portion 237 extends to the far surface of the housing 110, with threads sized to match the exterior threads on the retainer 140.

In a preferred embodiment, the outer portion of an end face 212 of the washer 210 is pressed axially against the flat surface 234 of a shoulder portion 233 of the hole 230 in the housing 110. The inner circumferential part of the washer face 211 is pressed against the window face 198. It can be suitable that the cross sectional dimensions of the axial holes through the washer, spacer, and threaded retainer are each slightly smaller than the smaller cross section portion of the window 190 (e.g., 12>D3 and D1>D4). This is believed to spread the axial force that the retainer applies to the window across the window's cross sectional area, thus reducing the chance of window breakage.

Some suitable sizes for the optical assembly components are: D1=0.25 inches, D2=0.375 inches; washer 210 and spacer: D3=0.23 inches; D4=0.55 inches; and retainer 140: D5=0.313 with 5/15 HEX internal shape. The HEX shape allows the retainer to be tightened into the threaded hole, holding the other optical components in place.

The threaded surface of the threaded portion 237 of the mating hole 230 can be drilled and tapped to form a desired length of internally threaded mating surface for the retainer 141. For example, in some applications, the threaded portion 237 of the hole 230 can be a ⅝ inch 18 UNF threaded portion, with an axial length of approximately 0.6 inches of interior threaded length, with a small unthreaded additional length 238 for holding the washer and spacer. The length and screw thread size and shape of the threaded portion 237 can be selected based on the strength requirements of the system.

In an exemplary embodiment, the washer 210, 211, spacer 150, 151, and retainer 140, 141 are formed of materials of increasing stiffness and increasing thickness. For example, the washers can be MYLAR, the spacers can be TORLON, and the retainers can be stainless steel. This allows the most compliant materials that are closest to the windows 190, 191 to be compressed slightly when the retainer is tightened, to avoid breaking the window while maintaining the window surface flush with the inner housing surfaces 111, 121. In particular, if optical components expand or contract along the axial x direction due to temperature or pressure changes, the expansion or compression is absorbed by the more compliant members, such as the o-ring, the washer, and the spacer.

Further, because expansion and contraction of the spacer, washer, and retainer in an axial direction will be absorbed by the compliant gaskets 200 and the washer 210, the axial movement of the window face 192 will be limited to that due to expansion or contraction of the smaller cross sectional area portion 197 of the window that is closest to the cavity 160. Because the window material has a low thermal expansion coefficient and a small Young's modulus, and because the axial length of this portion of the window is small, the displacement of the window surface is expected to be very small. In this example, the window surface 192 is maintained flush with the surface 111 of the housing 110 within a very small tolerance.

In the example discussed herein, the washer and spacer are separate components. It may also be suitable to use a single component formed by adhering a thin layer of compliant material to a spacer element, so the single spacer component includes both a thinner, more compliant layer intended to face the window and a thicker, less compliant layer intended to face the retainer.

Specific dimensions and materials for the optical components, the shim, the housings, and the mechanical attachment design details can be selected based on engineering requirements for a specific application. For example, a high pressure application might require that the threaded screws or bolts holding the housings 110 and 120 together not break, that the bolts that connect the housings 110, 120, and 130 together and/or to an external surface not fail, that the fluid at a particular pressure not leak past the seals, and that fluid cavity thickness be held at a particular range of values over a wide range of temperatures and pressures.

The components are typically assembled at atmospheric pressure, and later subjected to the high pressure fluid flow, with the system potentially being located at either low or elevated temperatures. To ensure that the fluid flow cavity remains within a particular range of thickness values for proper optical imaging of the entrained particles (e.g. the parts must remain stable within a small tolerance at elevated operating pressures), fasteners are selected on the basis of the their Young's modulus and cross sectional area, and their geometries are selected to control the elongation effects on the optical channel to within the established tolerance. Standard fasteners can be used if they meet the engineering requirements, or custom fasteners can be designed and manufactured.

Another aspect of material selection and design involves holding the assembly together against the high pressure fluid environment. The number, size, and type of mounting bolts and threaded screw attachments can be chosen to allow the system to withstand a high pressure fluid requirement without failure.

In this example, eight threaded screws are arranged outside the o-ring seals and have a mating fit with eight corresponding inside-threaded holes to hold the housings 110 and 120 together with the shim 170 between them during operation with high pressure fluid flowing through the cavity. In this example, four through-holes are provided at the corners and extend through the housings 110, 120, 130, and through the shim 170, which allows the entire assembly to be bolted together and/or attached to an external structure.

In operation, high pressure fluid enters through the inlet passageway 125, passes through the flow cavity 160, and exits the outlet passageway 126. As the fluid travels through the cavity, a light source directs light into the fluid through one of the optical windows 190, through the fluid, through the opposite window 191, and to an imaging device located external to the device 100 (not shown). In a preferred embodiment, the light is coherent laser light. The imaging device captures an image of the light as it passes through the fluid. One suitable imaging system is described in U.S. Pat. No. 5,572,320 to Reintjes et al., the entire disclosure of which is incorporated by reference herein in its entirety. The image can be used to determine the number, size, and type of particles in the fluid. It can be suitable to size the cavity so that the particles at any x-position in the cavity between the windows will be in the near-field focal plane of the imaging system. For example, a 100 micron thick flow cavity, with an F-6 imaging system, can allow particles between 4 microns and 100 microns to be in focus. The particles can be, for example, solid debris, contaminants, or wear particles from external machinery through which the fluid is flowing. With the use of different imaging sensors and imaging algorithms, even semi-solid particles such as biological components can be evaluated.

In this example, light passes through the window 190 in the housing 110, through the fluid viewing cavity 160, and through the window 191 in the opposite housing 120. Referring again to FIGS. 3A, 3B, 4A, and 4B, it is seen that an optional light directing module 130 is mounted at an opposite face of the housing 120 to direct the light back through the device to a camera or imaging sensor (not shown).

Figure 8A:
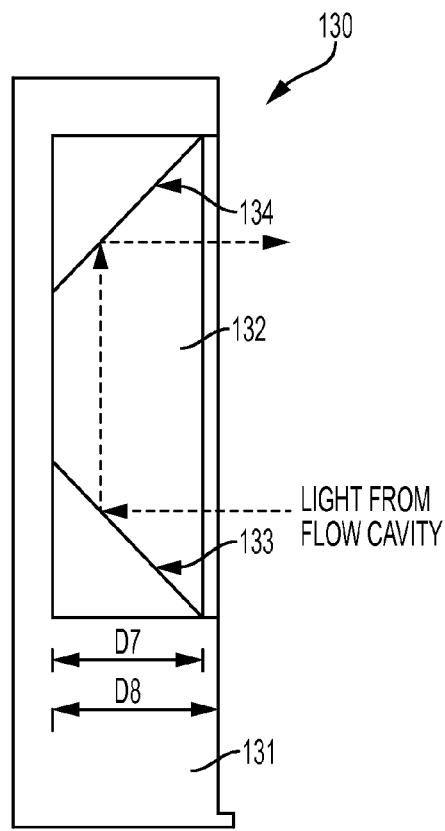
FIG. 8A-8D shows the optional light redirecting module in more detail.
Figure 8B:
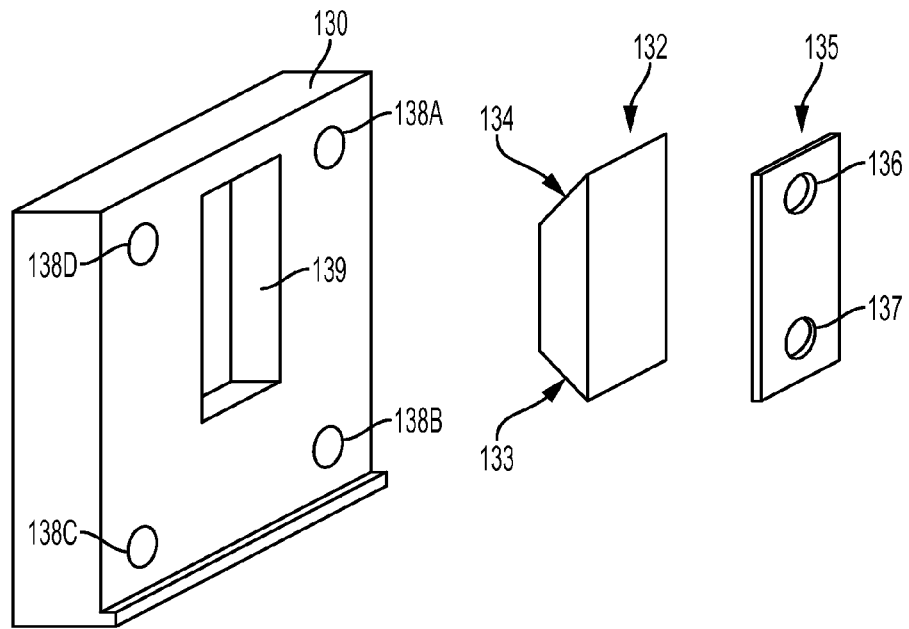

FIGS. 8A, 8B, 8C, and 8D show the light directing module 130 in more detail. As seen in FIG. 8A, in this example, the light directing module 130 can include a prism housing 131 and a dove prism 132, or other suitable retro reflecting device, adhered or otherwise attached within the housing 131. The dove prism has two reflective surfaces 133 and 134 that direct the light back along a path parallel to the incoming light path. The prism is formed of an optically transparent material such as glass.

In this example, the dove prism 132 has a depth dimension D7 that is slightly less than the depth dimension D8 of the cavity 139, forming a thin gap at the surface of the prism. The gap allows a prism spacer element 135 to be placed at the face of the prism 132 to protect the prism from contact with the very hard material of the adjacent housing 120. The prism spacer element 135 can be formed of a relatively compliant material that is unlikely to crush or scratch the prism, such as, for example, TORLON. Two through-holes 136 and 137 in the spacer element 135 allow the light to pass through the prism material to and from the reflective surfaces 133 and 134 without obstruction.

Figure 8D:
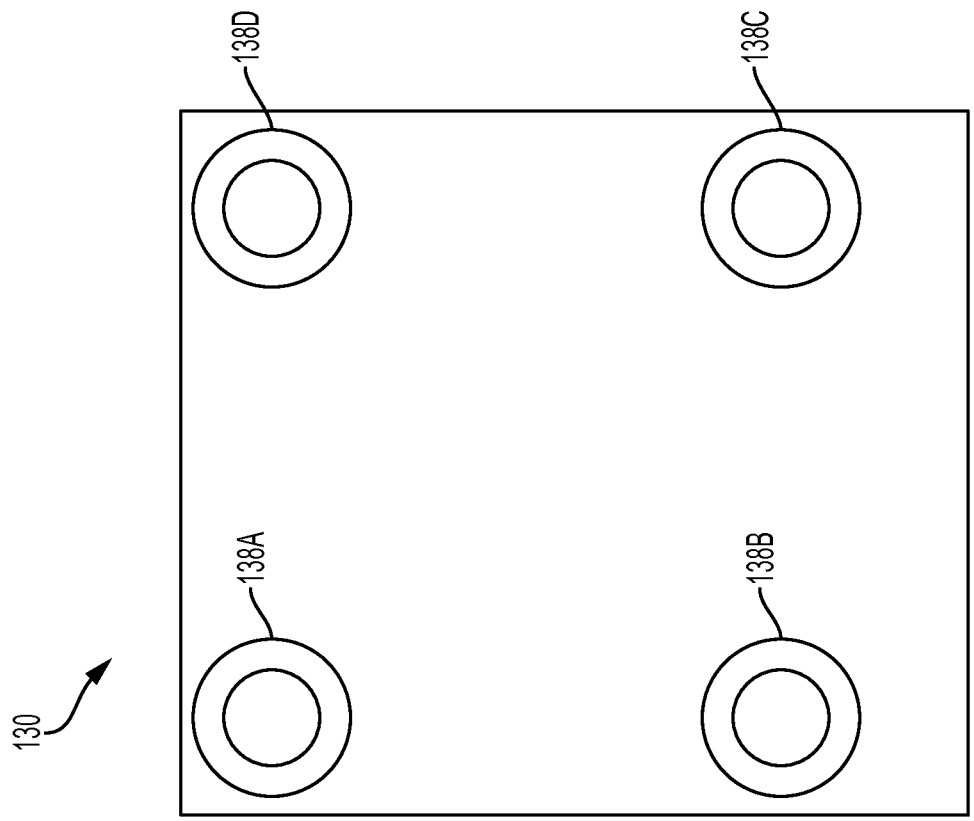
Figure 8C:
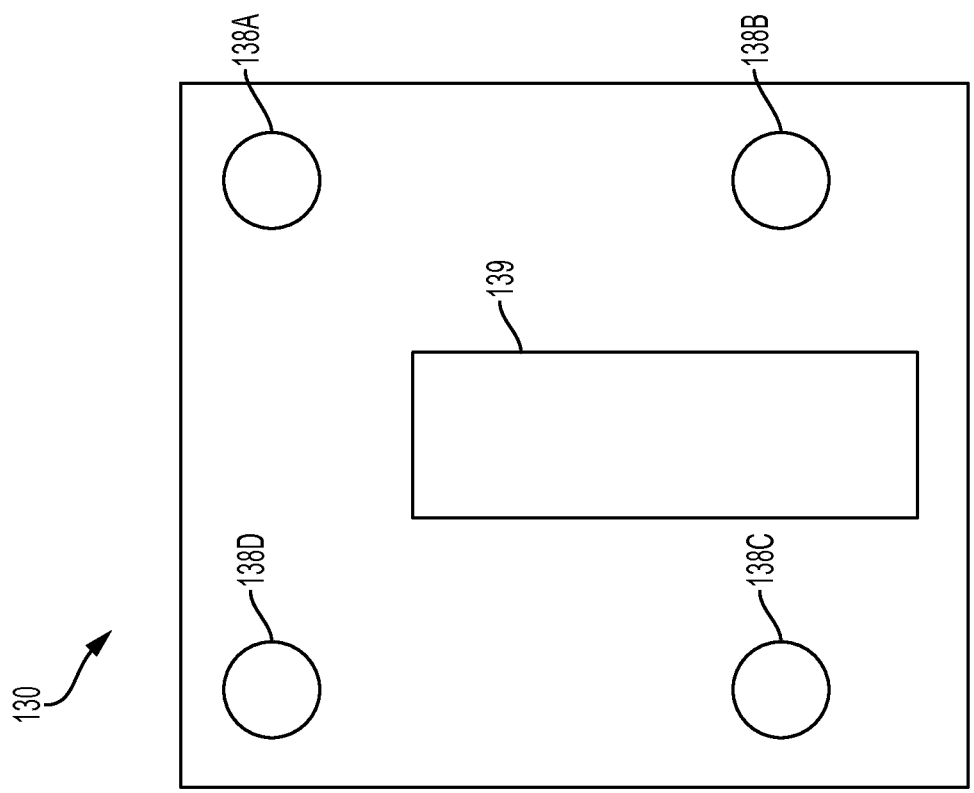

As seen in FIGS. 8C and 8D, four bolt holes can be provided generally at the corners of the module 130 that correspond to the four bolt holes in modules 110 and 120. These allow mechanical attachment of modules 110, 120, and 130 together, and/or attachment of the entire assembly to an external structure. Other mechanical attachment devices may also be suitable, depending on the specific design parameters discussed in earlier paragraphs.

The light directing module 130 is particularly suitable for locations and applications in which it is desired that the light source and camera or other imaging device should be positioned on the same side of the device, or in which the entire device is affixed to a mounting plate such that the imaging device cannot be located at the far side of the device. In applications in which a camera can be positioned at the far side of the device opposite the light source, the optional prism housing is not needed. The addition through-hole that extends through the housings 110 and 120 and the shim 170 for transmitting the light from the prism to the imaging system are also not needed in such a configuration.

The housings, shim, and mechanical attachment components of the system should be formed of materials that can withstand high pressure without failure, have a low thermal expansion coefficient, resist deformation due to high pressures (are stiff), are machinable, and have good resistance to corrosion and to the effects of the fluid passing through the device (e.g., oil or hydraulic fluid).

Figure 9:
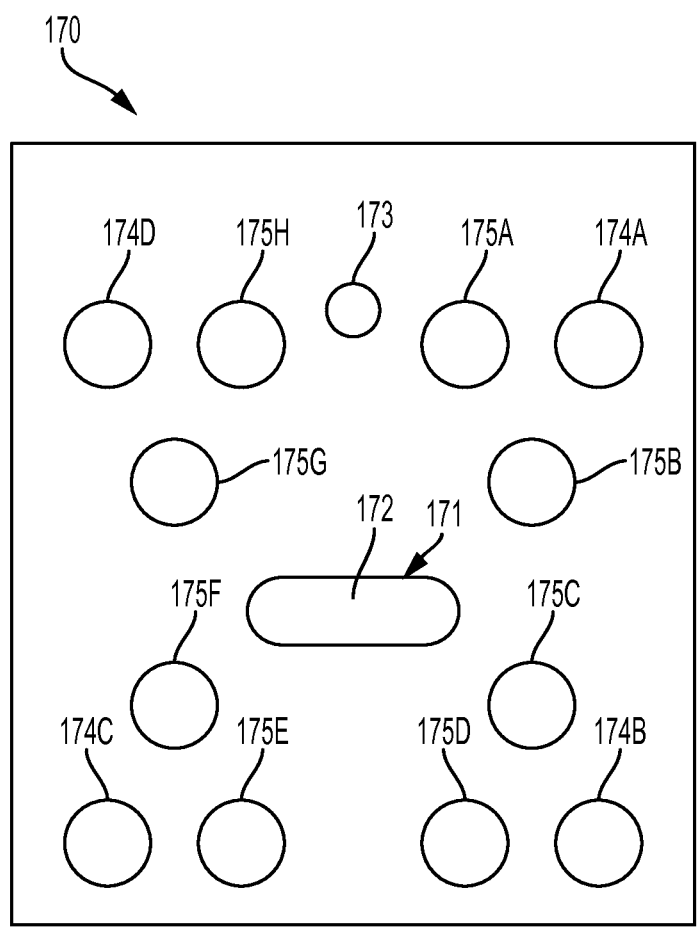
FIG. 9 shows the shim or gap spacer that is positioned between two of the housings in an exemplary embodiment.

FIG. 9 shows the optical cell spacer or shim 170 in more detail. The gap spacer can be stainless steel, for example, 316 stainless steel, or another suitable material. The thickness of the gap spacer 170 determines the thickness of the flow cavity 160. In this example, the thickness of the gap spacer can be about 0.004 inches. The hole 172 through the central portion of the gap spacer 170 aligns with and is slightly smaller than the o-ring grooves in the facing surfaces of the housings 110 and 120. A second hole 173 through the shim allows the light to pass through the shim after it has been redirected by the light directing module 130. Note that if the optional light redirecting module is not used, the hole 173 can be eliminated from the design.

The remaining holes are for the mechanical attachment screws and bolts that hold the housings and shim tightly together. The hole patterns in the spacer and the housings correspond to each other to allow the attachments to be made. In this example, the outer holes 174A, 174B, 174C, and 174D can correspond to through-holes in each of the housings 130, 120, and 110, to allow the entire assembly to be bolted together or bolted to an external structure. The eight other holes, 175A-175H, in this example, are used for screws or bolts to hold the shim tightly between the two housings 110 and 120. Different hole patterns for mechanical attachment systems may also be suitable for other designs, depending on the system requirements discussed in earlier paragraphs.

The shim thickness defines the thickness of the flow cavity. It is noted that hard particles having a size larger than the thickness dimension of the cavity will not pass through the cavity. It can be suitable, therefore, to install a filtration system upstream in the fluid flow to remove larger particles from the fluid flow, and/or to use a spacer with a thickness that is greater than the expected particle size.

By "high pressure", it is meant that the fluid pressure is at least 100 psi. The design shown herein can withstand much higher fluid pressures, however, in excess of one thousand psi.

Figure 10E:
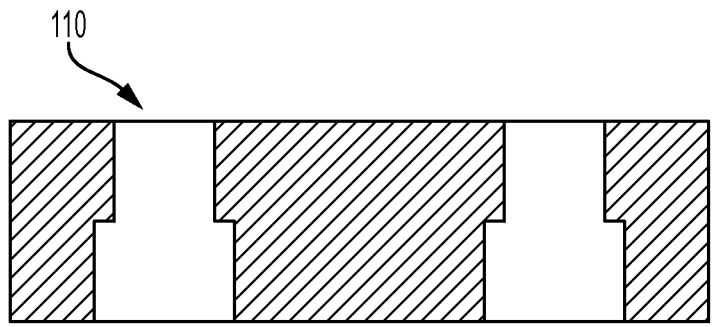
Figure 11E:
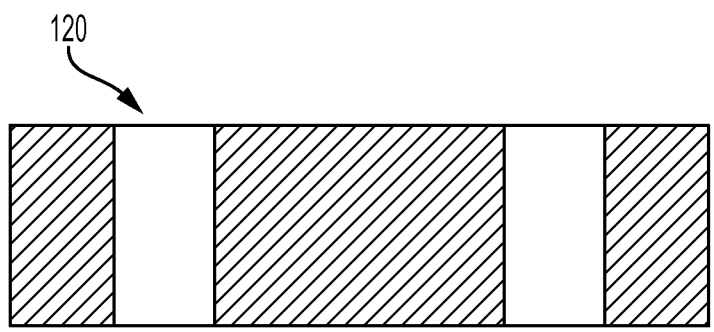

FIGS. 10A and 10C show the opposing faces of the first housing member 110, while FIGS. 10B, 10C, and 10D show cross sectional views through several sections of interest. FIGS. 11A and 11C show the opposing faces of the first housing member 120, while FIGS. 11B, 11C, and 11D show cross sectional views through several sections of interest.

The optical window is formed of a material that is transparent at the wavelength of the laser light source, and can be fused silica glass or another type of glass, transparent ceramic, or plastic or polymer having sufficient strength and transparency.

Alternative designs can also be suitable. For example, depressions can be machined into the faces 111, 121 of the housings 110 and/or 120 to form the optical flow cavity 160. In such an example, the shim 170 is not necessary. An advantage of including the shim 170 in the design described above is that the thickness of the optical flow cavity can be easily changed by simply replacing the shim with a shim with a different thickness shim. Another advantage is that it avoids having to accurately machine a very thin, planar depression in face of one or both of the housings 110 and 120.

Alternative materials may also be suitable. Stainless steel housings, shims, and mechanical fasteners are described above, selected both for their resistance to the corrosive effects of various fluids and for their strength. In less caustic or lower pressure environments, other metallic or non-metallic materials may be used.

Although optical assemblies are shown on both sides of the flow cavity in the examples above, in some applications, it may also be suitable to include only one optical assembly on one side, with a reflective surface provided on the opposite housing surface to reflect the light back through the flow, through the optical assembly, and to an external imaging system.

The example systems described herein can provide real time online optical analysis of fluid flow at high pressures in caustic environments. In comparison, the system described in U.S. Pat. No. 5,572,320 to Reintjes et al. provides real time online optical analysis of particles in flowing fluid, but is generally not suitable for fluid pressures over 100 psi. U.S. Pat. No. 8,056,400 to Reintjes et al. describes another system for particle-entrained fluid sampling, but similarly is generally not suitable for fluid pressures in excess of 100 psi.

Other advantages of this system include the easy disassembly and reassembly for cleaning, adjustment, or replacement of the optical components and the o-rings, and the ability to readily change the thickness of the flow cavity by swapping out the shim for one of a different thickness. The modularity of the system, with adapters for changing the flow and light directions, allows the system to be used in different configurations in spaces with different positional constraints.

It may also be suitable to use the housings, shim, and mechanical attachment devices together as an assembly for other flow sensing applications, by replacing or adding other types of sensors in place of or in addition to the optical window. For example, fiber optic sensors for temperature or pressure can be positioned with their faces at the surface of the cavity, in a manner similar to that described herein. Other sensors can be positioned in or adjacent to the fluid flow.

The invention has been described with reference to certain preferred embodiments. It will be understood, however, that the invention is not limited to the preferred embodiments discussed above, and that modification and variations are possible within the scope of the appended claims.

What is claimed as new and desired to be protected by Letters Patent of the United States is:

1. A high pressure cell for viewing high pressure fluid passing through the cell, comprising:
    a first housing member and a second housing member;
    a spacer member sandwiched between substantially planar surfaces of the first housing member and the second housing member, the spacer member having a thickness less than the first and second housing members,
    the spacer member having a hole therethrough with an edge of the hole defining a flow cavity between the first housing member and the second housing member;
    each of the first housing member and the second housing member having a groove for a gasket on a surface of the housing member that faces the spacer member, each groove surrounding and being larger than the hole through the spacer member;
    an inlet passage formed in either the first housing member or the second housing member extending from an outer face of the first or second housing member to the flow cavity;
    an outlet passage formed in either the first housing member or the second housing member and extending from an outer face of the first or second housing member to the flow cavity;
    an optical window in a mounting hole of the first housing member positioned with a surface of the optical window exposed to the flow cavity,
    wherein the at least one window has first portion at a first end with a substantially constant smaller cross sectional area, a second portion at a second end with a substantially constant larger cross sectional area, and a shoulder between the first and second portions, wherein the at least one window is positioned in the mounting hole with the first end facing the flow cavity;
    a compliant gasket positioned around the first portion of the window between the shoulder of the window and a corresponding first shoulder surface in the mounting hole; and
    an externally threaded retaining member having a central opening configured to let light pass through the retaining member along a main axis,
    the externally threaded retaining member being positioned in a threaded portion of the mounting hole, such that tightening the retaining member compresses the gasket against the first shoulder of the mounting hole, creating a static seal against fluid leaking past the window and positioning the window with an end face at the surface of the flow cavity.

2. The high pressure cell according to claim 1, further comprising:
    another optical window in a mounting hole of the second housing member positioned with a surface of the optical window exposed to the flow cavity, the optical windows being aligned on opposite sides of the flow cavity to transmit and receive light into and from the cavity, respectively.

3. The high pressure cell according to claim 2, wherein each window has a planar end surface that is flush with the surface of the adjacent housing member that faces the flow cavity.

4. The high pressure cell according to claim 1, wherein the inlet passageway has an opening to the flow cavity at an upstream location relative to the window, and the outlet passageway has an opening to the flow cavity at a downstream location relative to the window.

5. The high pressure cell according to claim 1, further comprising:
    mechanical attachment elements arranged to hold the first housing member, the spacer member, and the second housing member together when high pressure fluid passes through the cell.

6. The high pressure cell according to claim 5, wherein the mechanical attachment elements include threaded screws or bolts positioned in corresponding mating holes that extend entirely through the first housing member and at least partially through the second housing member.

7. The high pressure cell according to claim 6, wherein the number and size of threaded screws and bolts is determined based on the yield strength of the housing members and screws or bolts and the expected pressure of the fluid passing through the cell.

8. The high pressure cell according to claim 1, further comprising:
    a gasket positioned in each groove in the first and second housing members to form a static seal.

9. The high pressure cell according to claim 8, wherein the gasket is an o-ring.

10. The high pressure cell according to claim 8, wherein the grooves are elongated with a length greater than their width, or wherein the gasket and grooves have an oval shape.

11. The high pressure cell according to claim 1, further comprising:
    a light directing module attached to either the first housing member or the second housing member and having at least one reflector,
    wherein an optical path extends from the flow cavity to a reflector in the light directing module to direct light out of the cell.

12. The high pressure cell according to claim 11, wherein the at least one reflector is a dove prism positioned to receive light from the flow cavity after the light has passed through the flow cavity, and to direct the received light through openings in the first housing member and the second housing member to exit the cell, and the cell further comprising:
    a housing configured for mechanical attachment to either the first or second housing member to hold the dove prism in position.

13. The high pressure cell according to claim 12, wherein each of the first and the second housing members and the light directing module have a plurality of holes extending therethrough aligned with each other to receive mounting bolts or other connectors.

14. The high pressure cell according to claim 1, further comprising:
    a flat washer and a flat spacer positioned in the mounting hole, each of the washer and the spacer having a through hole that is smaller than the cross sectional dimension of the first portion of the window, the washer being positioned in the mounting hole between the window and the spacer, and the spacer being positioned in the mounting hole between the washer and the threaded retaining member, the washer being thinner and formed of a more compliant material than the spacer, and the spacer being thinner and formed of a more compliant material than the threaded retaining member, wherein tightening the retaining member compresses the washer and spacer against a second shoulder of the mounting hole, and compresses the gasket against the first shoulder of the mounting hole, creating a static seal and positioning the window with an end face at the surface of the flow cavity.

15. A method for illuminating high pressure flowing fluid in a high pressure cell, comprising:

providing the high pressure cell, including a first housing member and a second housing member, a spacer member held tightly between substantially planar surfaces of the first housing member and the second housing member, the spacer member having a thickness less than the first and second housing members, the spacer member having a hole therethrough with an edge of the hole defining a flow cavity between the first housing member and the second housing member, each of the first housing member and the second housing member having a groove for a gasket on a surface of the housing member that faces the spacer member, each groove surrounding and being larger than the hole through the spacer member, an inlet passage formed in either the first housing member or the second housing member extending from an outer face of the first or second housing member to the flow cavity, an outlet passage formed in either the first housing member or the second housing member and extending from an outer face of the first or second housing member to the flow cavity, an optical window in a mounting hole of the first housing member positioned with a surface of the optical window exposed to the flow cavity, wherein the at least one window has first portion at a first end with a substantially constant smaller cross sectional area, a second portion at a second end with a substantially constant larger cross sectional area, and a shoulder between the first and second portions, wherein the at least one window is positioned in the mounting hole with the first end facing the flow cavity, a compliant gasket positioned around the first portion of the window between the shoulder of the window and a corresponding first shoulder surface in the mounting hole, and an externally threaded retaining member having a central opening configured to let light pass through the retaining member along a main axis, the externally threaded retaining member being positioned in a threaded portion of the mounting hole, such that tightening the retaining member compresses the gasket against the first shoulder of the mounting hole, creating a static seal against fluid leaking past the window and positioning the window with an end face at the surface of the flow cavity;

introducing high pressure fluid into the flow inlet such that the fluid flows through the flow cavity and exits through the flow outlet; and directing light through the optical window into the high pressure fluid in the flow cavity.

16. The method according to claim 15, wherein the high pressure cell includes another optical window in a mounting hole of the second housing member positioned with a surface of the optical window exposed to the flow cavity, the optical windows being aligned on opposite sides of the flow cavity to transmit and receive light into and from the cavity, respectively.

17. The method according to claim 16, wherein each window has a planar end surface that is flush with the surface of the adjacent housing member that faces the flow cavity.

18. The method according to claim 15, wherein the inlet passageway has an opening to the flow cavity at an upstream location relative to the window, and the outlet passageway has an opening to the flow cavity at a downstream location relative to the window.

19. The method according to claim 15, wherein the spacer member is held tightly between the first and second housing members with threaded screws or bolts positioned in corresponding mating holes that extend entirely through the first housing member and at least partially through the second housing member.

20. The method according to claim 15, wherein a gasket is positioned in each groove in the first and second housing members to form a static seal, or an o-ring gasket is positioned in each groove in the first and second housing members to form a static seal.

21. The method according to claim 20, wherein the grooves are elongated with a length greater than their width, or wherein the gasket and grooves have an oval shape.

22. The method according to claim 15, further comprising:

transmitting the light, after it has passed through the optical cavity, into a light directing module having at least one reflector and mechanically attached to either the first housing member or the second housing member, and subsequently out of the cell.

23. The method according to claim 22, wherein the at least one reflector is a dove prism positioned to receive light from the flow cavity after the light has passed through the flow cavity, and to direct the received light through openings in the first housing and the second housing to exit the cell.

24. The method according to claim 22, wherein each of the first and the second housing members and the light directing module have a plurality of holes extending therethrough aligned with each other to receive mounting bolts or other connectors.

25. The method according to claim 15, wherein the high pressure flow cell includes a flat washer and a flat spacer positioned in the mounting hole, each of the washer and the spacer having a through hole that is smaller than the cross sectional dimension of the first portion of the window, the washer being positioned in the mounting hole between the window and the spacer, and the spacer being positioned in the mounting hole between the washer and the threaded retaining member, the washer being thinner and formed of a more compliant material than the spacer, and the spacer being thinner and formed of a more compliant material than the threaded retaining member, wherein tightening the retaining member compresses the washer and spacer against a second shoulder of the mounting hole, and compresses the gasket against the first shoulder of the mounting hole, creating a static seal and positioning the window with an end face at the surface of the flow cavity.

* * * * *